United States Patent [19]
Sneller et al.

[11] Patent Number: 5,234,422
[45] Date of Patent: Aug. 10, 1993

[54] ELASTICIZED SANITARY NAPKIN

[75] Inventors: Diane L. Sneller; June T. Brennock, both of Cincinnati; Carl L. Bergman, Loveland, all of Ohio

[73] Assignee: The Procter & Gamble Company, Cincinnati, Ohio

[21] Appl. No.: 811,348

[22] Filed: Dec. 20, 1991

[51] Int. Cl.⁵ ............................................. A61F 13/15
[52] U.S. Cl. ................................................ 604/385.2
[58] Field of Search ................ 604/358, 385.1, 385.2, 604/387

[56] References Cited

U.S. PATENT DOCUMENTS

| | | |
|---|---|---|
| 2,064,431 | 12/1936 | Jurgensen . |
| 3,575,174 | 4/1971 | Mogor ................... 604/385.1 |
| 3,658,064 | 4/1972 | Pociluyko ............... 604/385.2 X |
| 3,860,003 | 1/1975 | Buell . |
| 4,184,498 | 1/1980 | Franco ................... 604/387 X |
| 4,490,148 | 12/1984 | Beckestrom ............. 604/385 |
| 4,579,556 | 4/1986 | McFarland .............. 604/385 |
| 4,597,761 | 7/1986 | Buell ..................... 604/397 |
| 4,655,759 | 4/1987 | Romans-Hess et al. ... 604/385 |
| 4,668,230 | 5/1987 | D'amico et al. ......... 604/385 |
| 4,692,163 | 9/1987 | Widlund ................ 604/385 |
| 4,701,177 | 10/1987 | Ellis et al. ............. 604/385 |
| 4,758,240 | 7/1988 | Glassman ............... 604/379 |
| 4,758,241 | 7/1988 | Papajohn ............... 604/387 |
| 4,770,657 | 9/1988 | Ellis et al. ............. 604/385 |
| 4,911,701 | 3/1990 | Mavinkurve ............ 604/385.2 |
| 4,940,462 | 7/1990 | Salerno ................. 604/385.2 X |
| 5,032,121 | 7/1991 | Mokry .................. 604/385.2 X |
| 5,074,856 | 12/1991 | Coe et al. .............. 604/385.2 X |

FOREIGN PATENT DOCUMENTS

| | | |
|---|---|---|
| 0091412 | 10/1983 | European Pat. Off. . |
| 0164435 | 12/1985 | European Pat. Off. . |
| 1-02228 | 3/1989 | Japan ..................... 604/385.1 |
| 2142241 | 1/1985 | United Kingdom . |
| 2156681 | 10/1985 | United Kingdom . |
| 2168253 | 6/1986 | United Kingdom . |
| 2214057 | 8/1989 | United Kingdom ...... 604/385.1 |
| 2233235 | 1/1991 | United Kingdom . |

Primary Examiner—Randall L. Green
Assistant Examiner—Mary Beth O. Jones
Attorney, Agent, or Firm—Steven W. Miller; Monte D. Witte; Jack D. Schaeffer

[57] ABSTRACT

A unitary disposable absorbent article such as a catamenial pad or incontinent pad is provided with an elasticized side flap by operatively associating an elastic member on both the upper surface and the lower surface of the side flap. The elastic member is preferably joined to the inner surface of the side flap as well as the outer surface of the side flap by folding it about the distal edge of the side flap. In a preferred embodiment, the elastic member comprises an elastomeric laminate of an elastomeric layer and a coverstock layer, with the coverstock layer being on the outside of the product, so that the sanitary napkin is provided with soft longitudinal edges which contact the wearer during use. In addition, the elastomeric laminate provides relatively low tension that while raising the side flaps of the product to be a barrier against lateral leakage, also maintain the product in a shape which does not encourage fluid run-off or leakage at the ends of the pad as well as providing a bunching benefit.

8 Claims, 4 Drawing Sheets

ELASTICIZED SANITARY NAPKIN

FIELD OF THE INVENTION

This invention relates to unitary disposable absorbent articles, more particularly, catamenial pads or incontinent pads having elasticized side flaps.

BACKGROUND OF THE INVENTION

Unitary disposable absorbent articles such as catamenial pads or incontinent pads all have the same basic structure. An absorbent core is encased between a liquid pervious topsheet and a liquid impervious backsheet. Numerous variations of and elements in addition to the basic topsheet, backsheet, and absorbent core arrangements are known. Each additional element is usually directed to improving a specific characteristic of the catamenial pad or incontinent pad.

Disposable absorbent articles have been provided with elastic members to improve the side leakage performance of such products. U.S. Pat. No. 3,860,003, issued to Buell on Jan. 14, 1975, discloses elasticized disposable absorbent articles wherein an elastic member is positioned in the side flap of the product between the topsheet and the backsheet. The elasticized portion of each side flap is positioned sufficiently remote from the semi-rigid absorbent body to permit an elasticized contractible line through the side flap. The side flap is gathered by the elastic member such that a boat-like configuration for the pad is presented and the side flaps form a barrier along the edges of the product. In particular, FIG. 5 and FIG. 6 show incontinent pads having various shaped absorbent cores wherein an elastic member is positioned along the side edges of the product.

European Patent Application 0 091 412 A2, Widlund, published Oct. 12, 1983, adopts the configuration shown in the Buell '003 patent and specifically relates it to a feminine hygiene product. The Widlund application teaches a sanitary napkin with elastic means spaced from the core to thereby raise and form barriers against lateral leakage from the product. FIG. 1 of the Widlund patent shows the boat-like shape of the product with the side flaps forming lateral barriers to the flow of exudates.

U.S. Pat. No. 4,597,761 issued to Buell on Jul. 1, 1986, discloses an elasticized insert product for use as an incontinent pad or sanitary napkin having elastic in the side flaps. One or more elastic strands are positioned in the side flap to allow the product to assume the boat-like configuration shown in FIG. 1 with the side flaps extending upwardly to form barrier walls against lateral leakage.

U.S. Pat. No. 4,579,556 issued to McFarland on Apr. 1, 1986, further defines the Buell '003 concept for incontinent pads by creating a dual baffle structure at the edges. The impervious backing sheet is folded over the topsheet and the absorbent layer and fastened to the topsheet so that when the elastic contracts, the pad bows with the elasticized fold raising above the surface of the pad to form a baffle. A lower baffle is formed over the absorbent with the upstanding baffle containing the elastic.

U.S. Pat. No. 4,668,230 issued to D'Amico et al. on May 26, 1987, adopts the Buell '003 approach and the Widlund application approach by extending the elastics to the ends of the pad and allowing the pad to assume a cup-like or boat-like shape. In particular, the elastics are secured at one end of the pad and extend at least two-thirds of the length of the remainder of the pad to give the proper trough-like shape to the pad. However, side flaps that stand up are not created in the D'Amico et al. patent.

UK Patent Application 2 168 253A, Baird and Robert published on Jun. 18, 1986, discloses an incontinent pad or sanitary napkin provided with liquid impermeable upwardly folded side flaps. The side flaps are formed by extending the backsheet beyond the absorbent core along at least part of the lateral edges of the absorbent core. A seal is formed adjacent the side edge of the absorbent core to present a dual baffle against leakage in the sides of the pad.

U.S. Pat. No. 4,701,177 issued to Ellis et al. on Oct. 20, 1987, provides a pad that is generally thicker in the center portion than at the ends of the pad. The upstanding side portions in the middle of each longitudinal edge are in the area where the absorbent core is hourglass or narrower shaped. The pad is also curved into a boat-like shape to generally conform to the pudendum of the wearer. The elastic film members are secured in the side flap of the sanitary napkin or incontinent pad between the topsheet and the backsheet to form the upstanding baffles.

U.S. Pat. No. 5,032,121 issued to Mokry on Jul. 16, 1991 adopts the Buell '003 and Widlund approach by placing the elasticized baffles in an hourglass-shaped pad with an hourglass-shaped absorbent core. The sanitary napkin includes a pair of elastic members affixed between the cover and the backsheet outward of the seal line and aligned adjacent to the central portion of the core. The elastic members cause the pad to acquire a cup-shaped configuration which corresponds to the perineal area of the user.

Each of these patents are related to providing elasticization in a sanitary napkin or incontinent pad. In each of these concepts, the elastic members are positioned in the side flap between the topsheet and the backsheet to allow the side flap to be gathered and to form upstanding baffles along the side edges of the product to slow or stop the lateral flow of body exudates beyond the edge of the pad. However, each of these approaches suffer from the fact that the backsheet and topsheet edges of the product are allowed to contact the wearer during use. The tension created by the elastic members in contracting these portions of the topsheet and the backsheet create a relatively rough surface adjacent the skin which can rub or chafe the wearer. Further, it has been found that relatively high tensions within the side flaps of the absorbent core may further reduce wearer comfort as well as the inherent bunching of the product by the wearer squeezing the thighs together.

In catamenial pads it is particularly desirable to improve wearing comfort while preventing increased soiling of the garments surrounding the pad. It is also desirable to provide catamenial pads having soft lateral edges to increase the wearer's comfort.

Therefore, it is an object of the present invention to provide a disposable absorbent article providing improved protection against soiling while providing improved wearer comfort.

It is a further object of the present invention to provide an elasticized catamenial pad or incontinent pad that protects against lateral soiling while improving the wearer's comfort.

SUMMARY OF THE INVENTION

According to the present invention, a unitary disposable absorbent article such as a catamenial pad or incontinent pad is provided with an elasticized side flap by operatively associating an elastic member on both the upper surface and the lower surface of the side flap. The elastic member is preferably joined to the inner surface of the side flap as well as the outer surface of the side flap by folding it about the distal edge of the side flap. In a preferred embodiment, the elastic member comprises an elastomeric laminate of an elastomeric layer and a coverstock layer, with the coverstock layer being on the outside of the product, so that the sanitary napkin is provided with soft side edges which contact the wearer during use. In addition, the elastomeric laminate provides relatively low tension that while raising the side flaps of the product to be a barrier against lateral leakage, also maintain the product in a shape which does not encourage fluid run-off or leakage at the ends of the pad as well as providing a bunching benefit.

DETAILED DESCRIPTION OF THE INVENTION

As used herein, the term "absorbent article" refers to devices which absorb and contain body exudates, and, more specifically, refers to devices which are placed against or in proximity to the body of the wearer to absorb and contain the various exudates discharged from the body. The term "disposable" is used herein to describe absorbent articles which are not intended to be laundered or otherwise restored or reused as an absorbent article (i.e., they are intended to be discarded after a single use, and, preferably, to be recycled, composted or otherwise disposed of in an environmentally compatible manner). A "unitary" absorbent article refers to absorbent articles which are formed of separate parts united together to form a coordinated entity. A preferred embodiment of a unitary disposable absorbent article of the present invention is the catamenial pad, sanitary napkin 20, shown in FIG. 1. As used herein, the term "sanitary napkin" refers to an absorbent article which is worn by females adjacent to the pudendal region, generally external to the urogenital region, and which is intended to absorb and contain menstrual fluids and other vaginal discharges from the wearer's body (e.g., blood, menses). Interlabial devices which reside partially within and partially external of the wearer's vestibule are also within the scope of this invention. As used herein, the term "pudendal" refers to the externally visible female genitalia. It should be understood, however, that the present invention is also applicable to other feminine hygiene or catamenial pads such as pantiliners or other absorbent articles such as incontinent pads, and the like.

Figure 1:
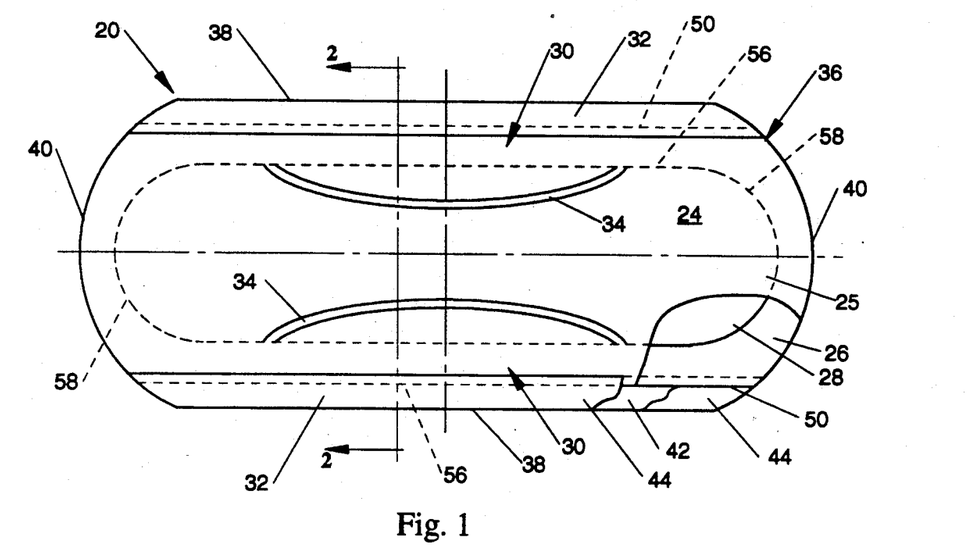
FIG. 1 is a plan view of a catamenial pad, sanitary napkin, according to the present invention.

FIG. 1 is a plan view of the sanitary napkin 20 of the present invention in its flat-out state with portions of the structure being cut-away to more clearly show the construction of the sanitary napkin 20 and with the portion of the sanitary napkin 20 which faces the wearer, facing the viewer. As shown in FIG. 1, the sanitary napkin 20 comprises a liquid pervious topsheet 24, a liquid impervious backsheet 26 joined with the topsheet 24, an absorbent core 28 positioned between the topsheet 24 and the backsheet 26, a side flap 30 extending outwardly from and along the side edges 56 of the absorbent core 28, elastic members 32 joined to the side flaps 30, and embossed channels 34.

FIG. 1 shows a preferred embodiment of the sanitary napkin 20 in which the topsheet 24 and the backsheet 26 have length and width dimensions generally larger than those of the absorbent core 28. The topsheet 24 and the backsheet 26 extend beyond the edges of the absorbent core 28 to thereby form not only the side flaps 30 but also portions of the periphery 36 of the sanitary napkin 20. The periphery 36 defines the outer perimeter or, in other words, the edges of the sanitary napkin 20. The periphery 36 comprises the longitudinal edges 38 and the end edges 40.

Figure 2:
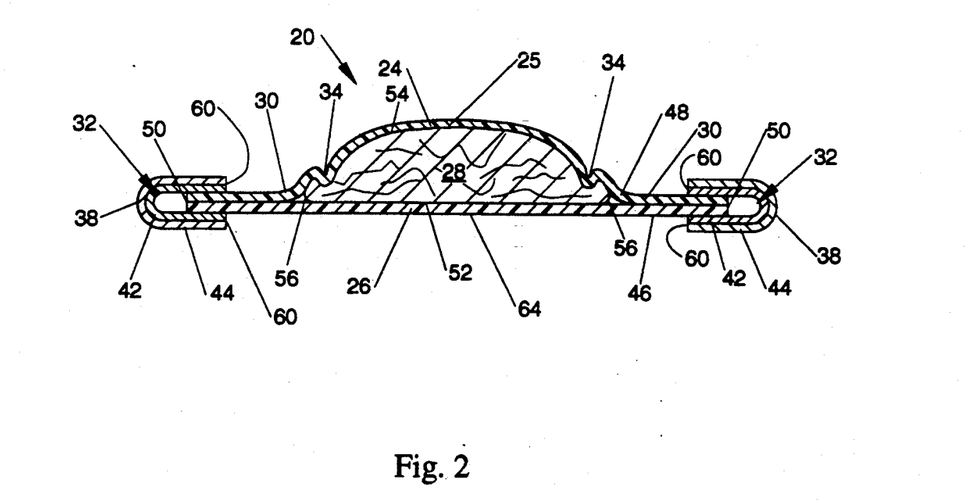
FIG. 2 is a cross-sectional view of the sanitary napkin taken along line 2—2 of FIG. 1.

FIG. 2 is a cross-sectional view of the sanitary napkin 20 taken along section line 2—2 of FIG. 1. FIG. 2 shows the topsheet 24 and the backsheet 26 extending laterally across the entire cross-section to form each side flap 30. The absorbent core 28 is generally shown in FIG. 2 as being thicker in the center than at its edges (i.e., profiled) and positioned between the topsheet 24 and the backsheet 26 such that the topsheet 24 and the backsheet 26 encase the absorbent core 28. The embossed channels 34 are shown in FIG. 2 as being a region of the sanitary napkin 20 wherein preferably both the topsheet 24 and the absorbent core 28 are compressed. The elastic members 32 are shown in FIG. 2 as comprising an elastomeric laminate comprising an elastomeric layer 42 and a coverstock layer 44. One portion of the elastic member 32 is secured to the outer surface 46 of the side flap 30 (i.e., the backsheet 26) with the other portion secured to the inner surface 48 of the side flap 30 (i.e., the topsheet 24) such that the elastic member 32 has been folded about the distal edge 50 of the side flap 30 such that the elastic member 32 forms the longitudinal edge 38 of the sanitary napkin 20. The contraction of the elastic member 32 will cause the side flaps 30 to stand-up (fold upwardly toward the topsheet 24) to form a wall that acts as a lateral barrier to the flow of menstrual fluids (See FIG. 3).

The absorbent core 28 may be any absorbent means which is capable of absorbing or retaining liquids such as vaginal fluids (e.g., menses) and other certain body exudates. As shown in FIGS. 1 and 2, the absorbent core 28 has a garment surface 52, a body surface 54, side edges 56 and pad edges 58.

The absorbent core 28 may be manufactured in a wide variety of sizes and shapes (e.g., rectangular, oval, hourglass, dog bone, asymmetric, etc.) and from a wide variety of liquid-absorbent materials commonly used in sanitary napkins and other absorbent articles such as comminuted wood pulp which is generally referred to as airfelt. Examples of other suitable absorbent materials include creped cellulose wadding, meltblown polymers including coform, cross-linked chemically modified cellulosic fibers, synthetic fibers, tissue including tissue wraps and tissue laminates, absorbent foams, absorbent sponges, superabsorbent polymers, absorbent gelling materials, or any equivalent material or combinations of materials, or mixtures of these. The configuration and construction of the absorbent core may also be varied (e.g., the absorbent core may have varying caliper zones, hydrophilic gradients, superabsorbent gradients, or lower density and lower average basis weight acquisition zones; or may comprise one or more layers or structures). The total absorbent capacity of the absorbent core should, however, be compatible with the design loading and the intended use of the sanitary napkin. Further, the size and absorbent capacity of the absorbent core may be varied to accommodate different uses such as incontinent pads, pantiliners, regular sanitary napkins, or overnight sanitary napkins.

An exemplary absorbent structure for use as the absorbent core of the present invention that has achieved wide acceptance and commercial success is described in U.S. Pat. No. 4,950,264 entitled "Thin, Flexible Sanitary Napkin" issued to Osborn III on Aug. 21, 1990. This patent is incorporated herein by reference. A preferred embodiment of the absorbent core has a generally rectangular shape with rounded ends such as shown in FIG. 1 (i.e., linear side edges 56 and arcuate pad edges 58). The absorbent core 28 preferably comprises comminuted wood pulp fibers, airfelt, that is profiled in the lateral direction and the longitudinal direction to be thicker in the central region of the absorbent core for improved absorbency and fit of the product.

The backsheet 26 and the topsheet 24 are positioned adjacent the garment surface 52 and the body surface 54, respectively, of the absorbent core 28 and are preferably joined thereto and to each other by attachment means (not shown) such as those well known in the art. For example, the backsheet 26 and/or the topsheet 24 may be secured to the absorbent core 28 or to each other by a uniform continuous layer of adhesive, a patterned layer of adhesive, or an array of separate lines, spirals, or spots of adhesive. Adhesives which have been found to be satisfactory are manufactured by H. B. Fuller Company of St. Paul, Minn. under the designation HL-1258 or H-2031. The attachment means will preferably comprise an open pattern network of filaments of adhesive as is disclosed in U.S. Pat. No. 4,573,986 entitled "Disposable Waste-Containment Garment", which issued to Minetola and Tucker on Mar. 4, 1986, and which is incorporated herein by reference. An exemplary attachment means of an open pattern network of filaments comprises several lines of adhesive filaments swirled into a spiral pattern such as illustrated by the apparatus and method shown in U.S. Pat. No. 3,911,173 issued to Sprague, Jr. on Oct. 7, 1975; U.S. Pat. No. 4,785,996 issued to Zieker, et al. on Nov. 22, 1978; and U.S. Pat. No. 4,842,666 issued to Werenicz on Jun. 27, 1989. Each of these patents are incorporated herein by reference. Alternatively, the attachment means may comprise heat bonds, pressure bonds, ultrasonic bonds, dynamic mechanical bonds, or any other suitable attachment means or combinations of these attachment means as are known in the art.

The backsheet 26 is impervious to liquids (e.g., menses and/or urine) and is preferably manufactured from a thin plastic film, although other flexible liquid impervious materials may also be used. As used herein, the term "flexible" refers to materials which are compliant and will readily conform to the general shape and contours of the human body. The backsheet 26 prevents the exudates absorbed and contained in the absorbent core 28 from wetting articles which contact the sanitary napkin such as pants, pajamas and undergarments. The backsheet may thus comprise a woven or nonwoven material, polymeric films such as thermoplastic films of polyethylene or polypropylene, or composite materials such as a film-coated nonwoven material. Preferably, the backsheet is a polyethylene film having a thickness of from about 0.012 mm (0.5 mil) to about 0.051 mm (2.0 mils). An exemplary polyethylene film is manufactured by Clopay Corporation of Cincinnati, Ohio, under the designation P18-0401. The size of the backsheet is dictated by the size of the absorbent core and the exact sanitary napkin design selected. In a preferred embodiment, the backsheet extends beyond the absorbent core a minimum distance around the entire sanitary napkin periphery.

The topsheet 24 is compliant, soft feeling, and non-irritating to the wearer's skin. Further, the topsheet 24 is liquid pervious permitting liquids (e.g., menses and/or urine) to readily penetrate through its thickness. For the present invention, a preferred topsheet comprises an apertured plastic film. Apertured plastic films, formed films, are preferred for the topsheet because they are pervious to such body exudates and yet non-absorbent. Thus, the surface of the formed film which is in contact with the body remains dry, thereby reducing body soiling and creating a more comfortable feel for the wearer. Suitable formed films are described in U.S. Pat. No. 3,929,135, entitled "Absorptive Structures Having Tapered Capillaries", which issued to Thompson on Dec. 30, 1975; U.S. Pat. No. 4,324,246 entitled "Disposable Absorbent Article Having A Stain Resistant Topsheet", which issued to Mullane and Smith on Apr. 13, 1982; U.S. Pat. No. 4,342,314 entitled "Resilient Plastic Web Exhibiting Fiber-Like Properties", which issued to Radel and Thompson on Aug. 3, 1982; and U.S. Pat. No. 4,463,045 entitled "Macroscopically Expanded Three-Dimensional Plastic Web Exhibiting Non-Glossy Visible Surface and Cloth-Like Tactile Impression", which issued to Ahr, Lewis, Mullane, and Ouellette on Jul. 31, 1984, each of which patents is incorporated herein by reference. The preferred topsheet for the present invention is the formed film described in one or more of the above patents and marketed on sanitary napkins by The Procter & Gamble Company as "DRI-WEAVE". Alternatively, the topsheet may be manufactured from a wide range of materials, such as porous foams; reticulated foams; or woven or nonwoven webs of natural fibers (e.g., wood or cotton fibers), synthetic fibers (e.g., polyester or polypropylene fibers), or combinations of natural and synthetic fibers.

In a preferred embodiment of the present invention, the body surface 25 of the formed film topsheet is hydrophilic. The hydrophilic body surface helps liquid to transfer through the topsheet faster than if the body surface 25 was not hydrophilic. This diminishes the likelihood that menstrual fluid will flow off the topsheet rather than being absorbed by the absorbent core. In a preferred embodiment, surfactant is incorporated into the polymeric materials of the formed film topsheet. A formed film topsheet with surfactant incorporated therein is described in U.S. patent application Ser. No. 07/794,745, P&G Case 4528, filed on Nov. 19, 1991 by Aziz, et al., which is incorporated herein by reference.

Alternatively, the body surface 25 of the topsheet can be made hydrophilic by treating it with a surfactant. The surfactant would be substantially evenly and completely distributed throughout the body surface 25 of the topsheet. This can be accomplished by any of the common techniques well-known to those skilled in the art. For example, the surfactant can be applied to the topsheet by spraying, by padding, or by use of transfer rolls.

A side flap 30 extends outwardly from and along each side edge 56 of the absorbent core 28. The side flaps 30 should be highly flexible and thus contractible so that the elastic members 32 may gather the side flap 30 so that the side flaps 30 stand up in an upward configuration. The side flaps 30 are that portion of the sanitary napkin 20 between the periphery 36 and the side edges 56 of the absorbent core 28. In a preferred embodiment, the side flaps 30 are formed from the extension of the backsheet 26 and the topsheet 24 from and along the side edges 56 of the absorbent core 28. Each side flap 30 has a distal edge 50, an inner surface 48 generally formed by the topsheet 24 and an outer surface 46 generally formed by the backsheet 26.

The sanitary napkin 20 also comprises an elastic member 32 operatively associated in each side flap 30 to provide an elastically extensible feature in the longitudinal direction that enhances the containment, fit and comfort of the sanitary napkin. The elastic members 32 impart an overall curvature to the sanitary napkin, especially the absorbent core 28, for improved fit. Further, the elastic members 32 are folded about the distal edge 50 of the side flap 30 such that the longitudinal edge 38 of the sanitary napkin 20 is formed by the soft, non-irritating coverstock layer 44 of the elastic member 32 so as to enhance the comfort of the product. Further, when the elastic members 32 are operatively associated in an elastically contractible condition, the elastic members 32 tend to gather or contract the side flap 30 into an upraised configuration to form a wall (lateral barrier) to the flow of exudates along the topsheet 24.

The elastic members 32 are operatively associated in the side flaps 30 by being folded about the distal edge 50 of the side flap 30. Preferably, the elastic members 32 are operatively associated by being folded about the distal edge 50 in an elastically contractible condition so that in a normally unrestrained configuration, the elastic members 32 effectively contract or gather the side flaps so as to dispose the side flaps in an upraised configuration to form walls along the longitudinal edges 38 of the sanitary napkin 20 to reduce side leakage. The elastic members 32 can be secured to the side flaps 30 in an elastically contractible condition in a number of ways such as is disclosed in U.S. Pat. No. 3,860,003 issued to Buell on Jan. 25, 1975, and which patent is incorporated herein by reference. For example, the elastic members may be stretched and secured to the side flaps while the side flaps are in an uncontracted condition. Alternatively, the side flaps may be contracted, for example by pleating, and the elastic members secured to the contracted side flaps while the elastic members are in their unrelaxed or unstretched condition. Further, the elastic members may comprise heat shrinkable elastomeric films secured to the side flaps in an "uncontracted" condition and then heated so as to cause the elastic members to contract and gather the side flaps. Additionally, the elastic member may be joined in a substantially untensioned (or tensioned) condition and then subjected to mechanical stretching sufficient to permanently elongate the nonelastic component(s) of the side flap and/or the elastic member (a "zero strain" laminate) such as is disclosed in U.S. Pat. No. 4,107,364 issued to Sisson on Aug. 15, 1978; U.S. Pat. No. 4,209,563 issued to Sisson on Jun. 24, 1980; and U.S. Pat. No. 4,834,741 issued to Sabee on May 30, 1989; each of which is incorporated herein by reference.

The elastic member 32 may be stretched to any length suitable to gather or contract the side flaps 30 without generating excessive forces that could adversely affect the skin of the wearer or the shape of the sanitary napkin. It is preferred that the elongation may be relatively small so as not to cause bowing of the ends of the sanitary napkin. Generally, the elastic may be stretched from about 5% to about 100%, more preferably from about 10% to about 25%. In a preferred embodiment, the elastic member is stretched about 12.5% (112.5% of its original length) and adhered to the outer surface 46 of the side flap 30, the backsheet 26, and then folded over in the stretched condition and adhered to the inner surface 48 of the side flap 30, the topsheet 24. (Alternatively, the elastic members 32 could be adhered to the inner surface 48, folded over the distal edge 50, and secured to the outer surface 46; or simultaneously secured to both surfaces by prefolding of the elastic member 32.) In addition, differential tension may be applied to the elastic member such that different length portions may have different application tensions. For example, the central portion of the elastic member could be applied at a higher tension than the two end portions such that the central portion gathers the side flap more than the end portions.

While the elastic members 32 are preferably secured in the central region of the sanitary napkin 20, the elastic members 32 may have any length, including extending the entire length of the sanitary napkin 20. Preferably, the elastic members 32 extend through about 50% to about 90% of the length of the sanitary napkin in its uncontracted state.

The width of the elastic members 32 may also be widely varied. The width of each elastic member 32 should be great enough for it to be folded about the distal edge 50 of the side flap 30. However, each portion of the elastic member may have its own width, although preferably, such as is shown in FIG. 2, the width of the elastic member joined to the inner surface 48 of the side flap 30 is about equal to the width of the elastic member joined to the outer surface 46 of the side flap 30. Alternatively, the portion of the elastic member 32 joined to the outer surface 46 of the side flap 30 may be greater or lesser in width than the portion joined to the inner surface 48. In one alternative embodiment, the entire width of the outer surface of the sanitary napkin 20 may comprise the elastic member 32 with the ends folded over and onto the inner surface 48 of the side flaps 30.

Since the width of the elastic members 32 may be varied, the longitudinal edges 60 of the elastic member 32 may also be positioned in various locations on the sanitary napkin 20. For example, the longitudinal edge 60 of the elastic member 32 positioned on the inner surface 48 of the side flap 30 may be positioned over the absorbent core 28, adjacent the side edge 56 of the absorbent core 28, or outward from the side edge 56 of the absorbent core 28. In addition, the other longitudinal edge 60 positioned on the outer surface 46 may also be positioned in any of these various locations. In a preferred embodiment, at least one of the longitudinal edges 60 is spaced outwardly from the side edge 56 of the absorbent core 28, preferably from about 0.25 mm to about 25 mm. More preferably, both longitudinal edges 60 are spaced outwardly from the side edge 56 of the absorbent core 28, most preferably by an equal amount such as is shown in FIG. 2. By spacing each of the longitudinal edges 60 of the elastic member 32 outwardly from the side edge 56 of the absorbent core 28, a hinge point is formed which allows the side flap 30 to fold upwardly to form the barrier wall as previously discussed herein.

Additionally, the width of the elastic member 32 along its length may be varied such that the width of the elastic member on the inner surface 48 of the side flap 30 may be wider in one or more areas. For example, the width of the elastic member may be greater in the central region of the sanitary napkin 20 than in the end regions to create a higher barrier wall in this region and a more aesthetically pleasing appearance (i.e., the sanitary napkin would have a scalloped edge).

As shown in FIG. 2, the elastic member 32 is operatively associated with the side flap 30 by securing it along its length on both surfaces of the side flap 30 with an elastic attachment means. While the elastic members 32 may be secured to each surface of the side flap 30 adjacent only two points of the elastic member 32 (e.g. only at or adjacent its two ends) or any other length, it is preferable to secure the entire length and width of the elastic member 32 to the side flap 30. The elastic attachment means herein are preferably a hot melt adhesive such as marketed by Findley Adhesives, Inc., Elm Grove, Wis. as Findley Adhesives 581 or a double sided adhesive tape such as marketed by the 3M Company, St. Paul, Minn. The elastic members 32 may also be secured to the side flaps 30 in any of several other ways known in the art such as by gluing, ultrasonic bonding, heat/pressure bonds, dynamic mechanical bonds or the like.

In the embodiment illustrated in FIG. 1, the elastic members 32 extend about 80% of the length of the sanitary napkin when measured in an untensioned condition. Alternatively, the elastic members may extend the entire length of the sanitary napkin, or any other length suitable to provide the stand-up side flaps as discussed herein. A preferred elastic member has an uncontracted length and width of about 20 cm (8 inches) by about 3.0 cm (1.125 inches), respectively, and is folded about the distal edge 50 so that equal portions (about 15 mm) are positioned on the inner surface 48 and the outer surface 46 of the side flap 30. The elastic member 32 is applied in a stretched condition with a stretched length of preferably about 22.5 cm (9.0 inches). The longitudinal edges 60 of the elastic member 32 are preferably spaced outwardly from the side edge 56 of the absorbent core by about 3 mm.

Although the elastic member 32 can comprise a single layer of elastic material such as an elastomeric nonwoven material, preferred elastic members for the present invention comprise an elastomeric laminate comprising an elastomeric layer 42 and a coverstock layer 44. An elastomeric laminate provides a soft comfortable surface which is not irritating to the wearer's skin so as to provide a relatively soft longitudinal edge 38 for the sanitary napkin 20. The elastomeric laminate preferably comprises at least two elements: an elastomeric layer 42 and a coverstock layer 44. Alternatively, the elastomeric laminate may comprise more than two layers such as a tri-laminate of a coverstock layer, a second coverstock layer, and an elastomeric layer positioned between the coverstock layer and the second coverstock layer; or any other number of layers or arrangement of layers as required.

The elastomeric layer 42 may comprise a number of different elastic materials. For example, the elastomeric layer 42 may comprise elastomeric films (including heat shrinkable elastomeric films), "live" elastics of synthetic or natural rubber including films or strands of such elastic material, elastomeric foams (e.g., synthetic or natural rubber foams), elastomeric woven or nonwoven webs, formed elastic scrim, elastomeric adhesive, or other elastomeric materials as are known in the art. Preferably, the elastomeric layer 42 comprises an elastomeric film such as is marketed by Exxon of Paramus, N.J. under the designation EXX 500 1.5 mil elastic. In addition, the elastomeric layer 42 may take a multitude of configurations, sizes, and shapes. For example, the width of the elastomeric layer may be varied so as to comprise an overall film or may comprise one or more strands of elastic.

The coverstock layer(s) 44 may be any layer which is soft feeling and non-irritating to the wearer's skin. Suitable materials for the coverstock layer 44 include those materials suitable for use as the topsheet 24. In a preferred embodiment, the coverstock layer 44 comprises a non-woven web of synthetic fibers such as the nonwoven web marketed by Veratec of Walpole, Mass. under the designation DE 6957. Preferably, the coverstock layer 44 is a hydrophobic material so that fluids contacting the elastic member 32 will not wick outward to the periphery 36 of the sanitary napkin 20.

The elastomeric layer 42 is operatively associated with the coverstock layer(s) 44, preferably in an elastically contractible condition, more preferably prior to application of the laminate to the side flap 30, such that a gathered laminate is formed prior to assembly of the sanitary napkin so that the coverstock layer 44 is gathered prior to and after such assembly. In a preferred embodiment, the elastomeric layer 42 is operatively associated while being stretched from about 2 to 3 times its original length. The elastomeric layer 42 is secured to the coverstock layer 44 with an elastic attachment means (not shown) such as was previously discussed. The elastic attachment means are preferably an adhesive such as manufactured by Findley Adhesives, Inc. of Wauwatosa, Wis. under the designation Findley H2031. The elastic attachment means may also comprise any other attachment means such as ultrasonic bonds, heat/pressure bonds, dynamic mechanical bonds or any other means as are known in the art.

The elastic member 32 is operatively associated with the side flap 30 by folding the elastic member 32 about the distal edge 50 of the side flap 30. In a preferred embodiment, the elastic member 32 is operatively associated with the side flap 30 by securing a portion of the elastic member 32 to the outer surface 46 of the side flap 30, the backsheet 26, preferably while in a stretched condition, and folding the other portion over on top of the inner surface 48 of the side flap 30 and securing that portion to the side flap 30. Thus, the elastic member 32 is folded over the distal edge 50 of the side flap 30 and forms a portion of the longitudinal edge 38 of the sanitary napkin 20. Since the coverstock layer 44 is soft and non-irritating to the wearer's skin, a soft, non-wicking, longitudinal edge 38 for the sanitary napkin 20 is presented. Further, since the elastic member 32 comprises an elastomeric laminate, the elastic member 32 is relatively thick (i.e., has a larger caliper) such that it acts somewhat as a dam or dike for fluids flowing along the body surface 25 of the topsheet 24 so that fluids encounter the relatively high side wall of the elastic member 32 and are slowed so as to allow the absorbent core 28 time to absorb the fluid.

The sanitary napkin 20 also further preferably comprises a pair of embossed channels 34 positioned in the central region of the sanitary napkin 20 through preferably both the absorbent core 28 and the topsheet 24. The embossed channels 34 provide a contoured line that in combination with the elastic members 32 create a weakened area that enhances "controlled bunching" of the sanitary napkin. The embossed channels 34 also provide a stiffened edge or hinge for the elastic members to work against to allow the elastic edges to flatten out over the edge of the panty elastics, thereby providing added area coverage along the longitudinal edges 38 of the sanitary napkin 20. The embossed channels 34 preferably comprise densified or compressed regions within at least the absorbent core 28 that provide the functions hereinbefore described. In a preferred embodiment of the present invention as shown in FIG. 1, both the topsheet 24 and the absorbent core 28 are embossed so as to form the embossed channels 34. Examples of such embossed channels are disclosed in U.S. Pat. No. 3,575,174 issued to Mogor on Apr. 20, 1971 and U.S. Pat. No. 4,059,114 issued to Richards on Nov. 22, 1977, each of which is incorporated herein by reference.

Figure 3:
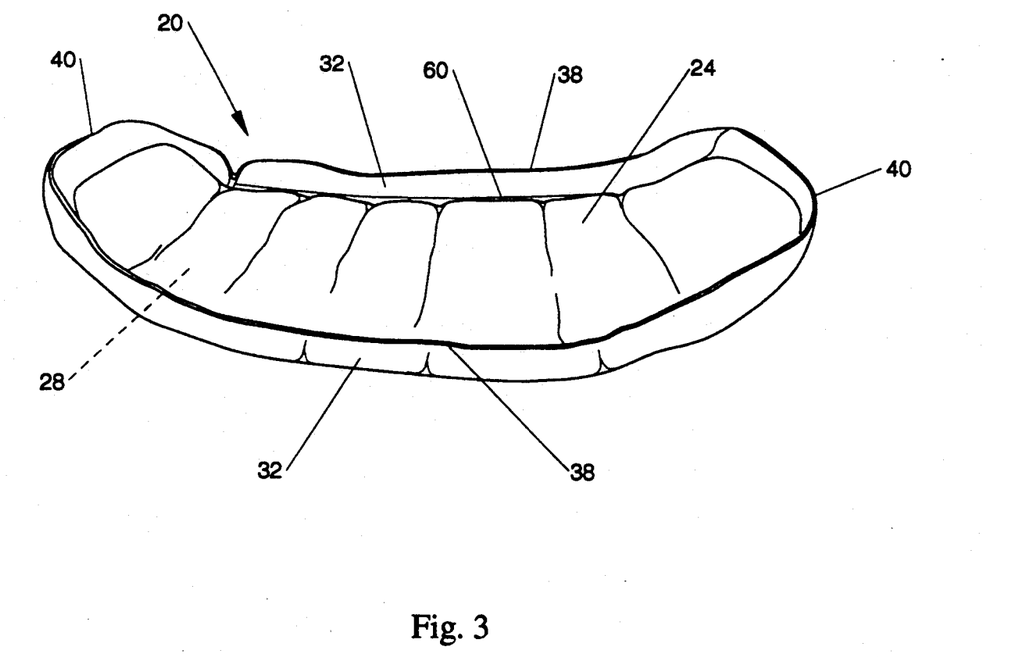
FIG. 3 is a perspective view of the sanitary napkin according to the present invention.

FIG. 3 shows a perspective view of the sanitary napkin 20 of the present invention in its contracted state. As shown in FIG. 3, the elastic members 32 act to contract or gather the side flaps 30 so that the side flaps 30 stand up in an upward configuration. At the same time, the elastic members 32 impart an overall curvature to the sanitary napkin. With this cuplike configuration, a reservoir capable of holding menstrual fluid at incidences of large flow are provided which allow the time necessary for the absorbent core 28 to fully absorb menstrual fluid. Further, the thickness of the elastic members provide a barrier wall along the longitudinal edges 38 of the sanitary napkin 20 that direct fluid back into the absorbent core 28 and also are hydrophobic so as to prevent the wicking of menstrual fluid out to the edges of the sanitary napkin 20. The embossed channels 34 allow the sanitary napkin 20 to conform to the body of the wearer when the thighs press against the longitudinal edges 38 of the sanitary napkin 20 to control bunching of the product so that the sanitary napkin fits snugly and comfortably to the wearer. Also, the longitudinal edges 38 of the sanitary napkin are resilient so as to bounce back to provide panty coverage, specifically coverage of the panty elastic even when the absorbent core gets bunched.

In use, the sanitary napkin 20 can be held in place by any support means (not shown) well-known for such purposes. Preferably, the sanitary napkin is placed in the user's panty and secured thereto by an adhesive. The adhesive provides a means for securing the sanitary napkin in the crotch portion of the panty. Thus, the outer surface 64 of the backsheet 26 is coated with an adhesive. Any adhesive or glue used in the art for such purposes can be used for the adhesive herein, with pressure-sensitive adhesives being preferred. Suitable adhesives are Century A-305-IV manufactured by the Century Adhesives Corporation, Instant Lock 34-2823 manufactured by the National Starch Company, and preferably 3 Sigma 3153 manufactured by 3 Sigma. Before the sanitary napkin is placed in use, the pressure-sensitive adhesive is typically covered with a removable release liner in order to keep the adhesive from drying out or sticking to a surface other than the crotch portion of the panty prior to use. Any commercially available release liners commonly used for such purposes can be utilized herein. Non-limiting examples of suitable release liners are BL30MG-A Silox E1/0 and BL30MG-A Silox 4P/O both of which are manufactured by the Akrosil Corporation. The sanitary napkin 20 of the present invention is used by removing the release liner and thereafter placing the sanitary napkin in a panty so that the adhesive contacts the panty. The adhesive maintains the sanitary napkin in its position within the panty during use.

Figure 4:
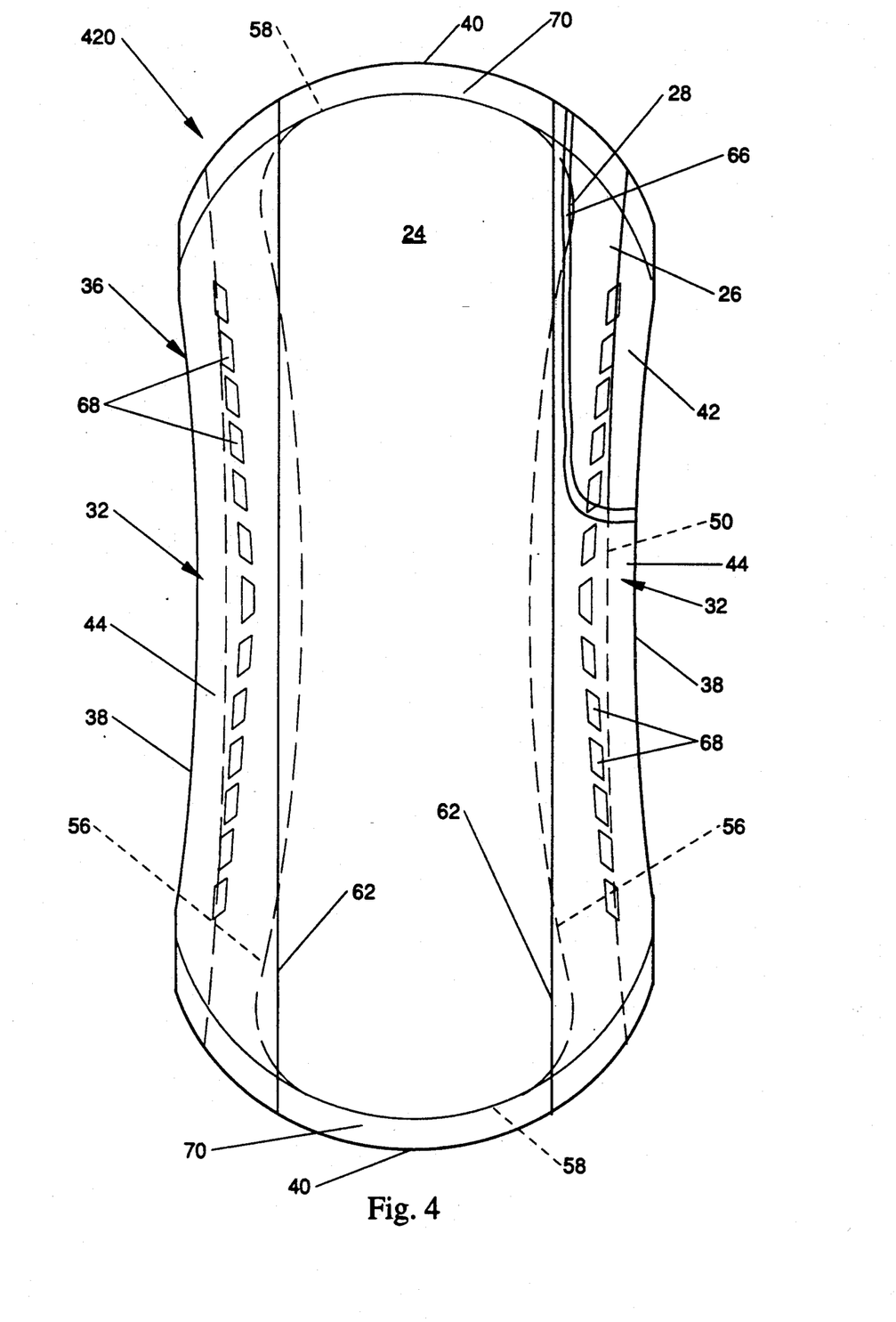
FIG. 4 is a plan view of an alternative embodiment of a sanitary napkin of the present invention.

FIG. 4 is a plan view of an alternative embodiment of the present invention, sanitary napkin 420. As shown in FIG. 4, the sanitary napkin 420 has a generally hourglass shape (hourglass-shaped chassis) such that it is narrower in its central region than in the ends. The sanitary napkin 420 comprises a topsheet 24 preferably configured as an overwrap layer 66, a backsheet 26, an absorbent core 28, side flaps 30, elastic members 32, side seals 68 and end seals 70. The absorbent core 28 preferably has an hourglass shape. The end seal 70 extends longitudinally from the pad edge 58 of the absorbent core 28 to the end edge 40 of the sanitary napkin and laterally from the longitudinal edge 38 to the other longitudinal edge 38, preferably in a curvilinear pattern generally corresponding to the shape of the absorbent core 28. The end seal 70 flattens the ends of the sanitary napkin, secures the ends of the elastic member 32 to the sanitary napkin, and "deadens" or deactivates the elastic member 32 for improved fit and containment. Thus, the end seal 70 prevents curling of the ends of sanitary napkin as well as anchoring of the elastic member 32. The side seal 68 is positioned outward from the side edge 56 of the absorbent core 28. The side seal 68 generally comprises a line or series of line segments that is preferably curvilinear in shape and that more preferably is generally parallel to the side edge 56 of the absorbent core 28. Thus, as shown in FIG. 4, the side seal 68 has an arcuate geometry that follows the side edge 56 of the absorbent core 28. This side seal design together with the contraction of the elastic member 32 differentially "pulls-in" the longitudinal edges 38 of sanitary napkin 420, with the greatest degree of pull-in occurring at the central portion of the sanitary napkin giving the sanitary napkin an even more defined narrower central portion.

Figure 5:
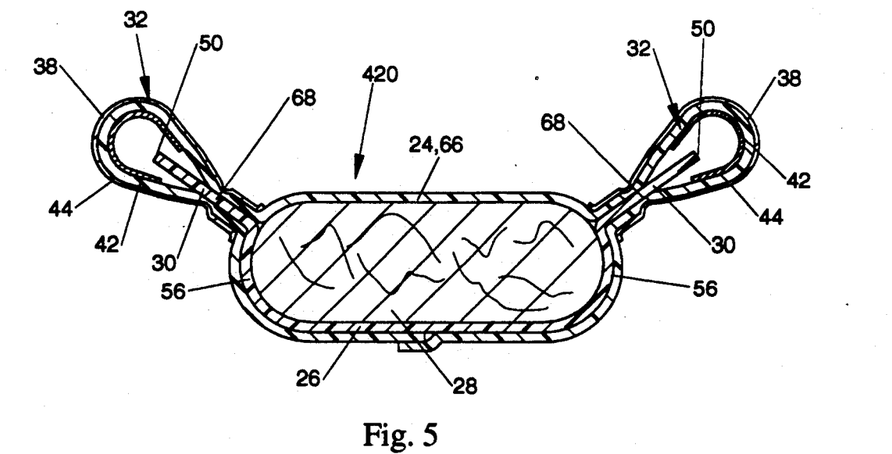
FIG. 5 is a cross-sectional view showing the alternative embodiment of the sanitary napkin shown in FIG. 4.

FIG. 5 shows a cross-sectional view of the construction of the sanitary napkin 420 shown in FIG. 4. The sanitary napkin 420 comprises the absorbent core 28 and the liquid impervious backsheet 26 covering the garment surface 52 of the absorbent core 28 and extending outwardly beyond the side edges 56 of the absorbent core 28 to form the side flaps 30. In this embodiment, the elastic member 32 comprises an elastomeric layer 42, a portion of the overwrap layer 66, and a coverstock layer 44. (The elastic member 32 alternatively need not comprise the overwrap layer 66 such that the topsheet 24 extends to or inward from the distal edge 50 such as is shown in FIG. 1.) The elastic member 32 is preferably joined to the side flap 30 only at the end seals 70 and the side seal 68 so that a gap may develop between the backsheet 26, the side flap 30, and the elastic member 32 in use. The elastic member 32 also preferably has the coverstock layer 44 and the overwrap layer 66 extend laterally inward from the longitudinal edges of the elastomeric layer 42 so that the elastomeric layer 42 is not secured to the side flap 30 by the side seal 68. The elastic member 32 is joined to the sanitary napkin, in this embodiment, by securing the elastomeric layer 42 to the overwrap layer 66 and by securing the coverstock layer 44 to the opposite side of the overwrap layer 66, folding the elastic member 32 over the distal edge 50 of the side flap 30, and securing the elastic member 32 to the sanitary napkin at the side seal 68 and the end seal 70. The elastomeric layer 42 preferably comprises a heat shrinkable elastomeric film. The overwrap layer 66 acts as the topsheet of the sanitary napkin; a soft, non-irritating overwrap layer adjacent the garment surface of the sanitary napkin; and a portion of the elastic member 32. (Any material suitable for use as the topsheet may also be used as the overwrap layer with formed thermoplastic films, more particularly Dri-Weave, being especially preferred.) The overwrap layer 66 is secured to itself adjacent the backsheet 26. The coverstock layer 44 is preferably a hydrophobic, quilted (embossed) nonwoven that has a high loft to provide a soft, cushioning effect. An exemplary example of such a quilted nonwoven is manufactured by Veratec of Walpole, Mass. under the designation P-11.

As shown in FIG. 5, the side seal 68 seals only the overwrap layer 66 and the coverstock layer 44 of the elastic member 32 to the side flap 30 between the side edge 56 of the absorbent core 28 and the longitudinal edges of the elastomeric layer 42. The side seal 68 preferably does not seal the elastomeric layer 42 to the side flap 30. The side seal 68 along with the "free floating" elastomeric layer 42 thus creates the soft, cushiony, "teardrop"-shaped cuff design shown in FIG. 5. This cuff design is resilient and soft so that the cuff retains its shape even under severe bunching. Further, because the elastic member 32 is anchored at its ends by the end seal 70, the cuff has less of a tendency to fold over onto the topsheet or under the side flap 30.

In use, the sanitary napkin 420 will assume a "W"-shaped cross-section in which the side flaps 30 are angled upward from the plane of the top surface of the sanitary napkin by preferably about 30° to 45°. This configuration is achieved by forming the side seal 68 adjacent the top surface plane. (This process is also called topsheet level or zero plane sealing or crimping.) In the Z-direction, the zero plane side seal helps keep the elasticized side flap 30 at or above the plane of the topsheet 24 resulting in better overall coverage of the panty of the wearer, creation of a stand-up barrier flap, as well as a slight "cupped" appearance of the sanitary napkin without excessive curvature.

Figure 6:
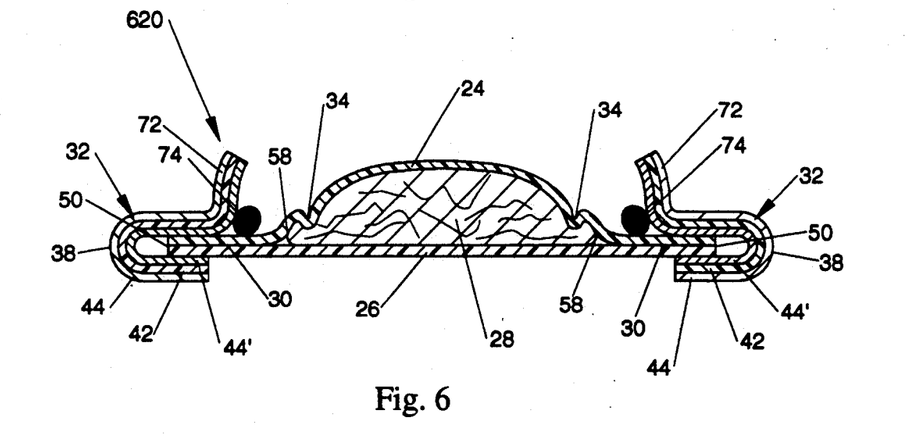
FIG. 6 is a cross-sectional view of a further alternative embodiment of the sanitary napkin of the present invention.

FIG. 6 shows a further alternative embodiment of the present invention wherein a barrier cuff 72 is formed along the sides of the sanitary napkin 620. The sanitary napkin 620 is similar to that shown in FIGS. 1-3 except that a segment of the elastic member 32 positioned on the inner surface 48 of the side flap 30 is not secured to the side flap 30. This unsecured portion (barrier cuff 72) is allowed to stand-up away from the body surface 25 of the topsheet 24 to present a barrier to the lateral flow of exudates from the sanitary napkin 620. Because the elastic member 32 is preferably operatively associated with the side flap 30 in an elastically contractible condition, the barrier cuff 72 is elasticized so as to contract and gather and stand upward away from the body surface 25. A spacing member 74 is also provided so that the barrier cuffs 72 are not compressed in a manner which collapses them. This spacing member 74 may comprise a number of different elements including a member positioned between the barrier cuff 72 and the topsheet 24. As shown in FIG. 6, the spacing member 74 is a relatively thick cylindrically shaped high loft nonwoven or foam material. Alternatively, the flap may be folded back upon itself at each end of the sanitary napkin 620 and secured with the end seal 70. A more detailed description of a barrier cuff as described herein is found in U.S. Pat. No. 5,026,364 issued to Robertson on Jun. 25, 1991, which patent is incorporated herein by reference.

Figure 7:
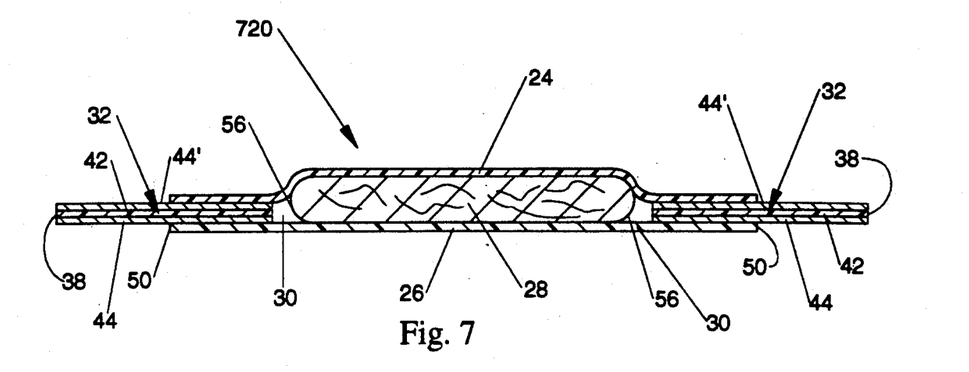
FIG. 7 is a cross-sectional view of a still further alternative embodiment of a sanitary napkin.

FIG. 7 is a further alternative embodiment of the present invention in which the problem of harsh longitudinal edges is solved by extending the relatively soft elastic member 32 beyond the distal edge 50 of the side flaps 30. As shown in FIG. 7, the sanitary napkin 720 comprises a topsheet 24, a backsheet 26, an absorbent core 28, a side flap 30, and an elastic member 32. The side flap 30 is preferably formed by extending the topsheet 24 and the backsheet 26 beyond the side edge 56 of the absorbent core 28. The elastic member 32 is joined between the topsheet 24 and the backsheet 26 with the a portion of the elastic member 32 extending laterally outwardly beyond the distal edge 50 of the side flap 30. The elastic member 32 may comprise any soft elastomeric material such as an elastomeric nonwoven or foam. Preferably, the elastic member 32 comprises an elastomeric laminate such as the tri-laminate shown in FIG. 7 as comprising a coverstock layer 44, a second coverstock layer 44′, and an elastomeric layer 42, preferably an elastomeric film, positioned between and operatively associated with the coverstock layers.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A unitary disposable absorbent article comprising:
   a liquid pervious topsheet;
   a liquid impervious backsheet joined with said topsheet;
   an absorbent core having side edges and positioned between said topsheet and said backsheet;
   a side flap extending outwardly from and along each side edge of said absorbent core, each said side flap having an inner surface, an outer surface, and a distal edge;
   an elastic member operatively associated with each said side flap by being folded about said distal edge of said side flap such that a portion of said elastic member is secured to the outer surface of said side flap and another portion is secured to the inner surface of said side flap, said elastic member comprising an elastomeric laminate comprising an elastomeric layer and a coverstock layer, said elastomeric layer being positioned adjacent said side flap such that said coverstock layer forms a portion of the outer surface of the absorbent article, the longitudinal edges of said coverstock layer extending laterally inward from the longitudinal edges of said elastomeric layer;
   a side seal joining a portion of said coverstock layer to said side flap, said side seal being positioned between said side edge of said absorbent core and the longitudinal edges of said elastomeric layer; and end seals joining said elastomeric layer and said coverstock layer to said side flaps.

2. The absorbent article of claim 1 wherein said side flap comprises a portion of said topsheet and a portion of said backsheet.

3. The absorbent article of claim 1 wherein said side flap comprises a portion of said backsheet, wherein said topsheet is formed from a portion of an overwrap layer, and wherein said elastic member comprises a portion of said overwrap layer.

4. The absorbent article of claim 1 wherein said side seal is formed along said topsheet.

5. The absorbent article of claim 4 having an hourglass shape, said absorbent core having a generally hourglass shape, and said side seal is generally parallel to said side edge of said absorbent core.

6. The absorbent article of claim 5 wherein said elastomeric layer is joined to said side flap only at said end seals.

7. The absorbent article of claim 6 wherein said elastomeric layer comprises a heat shrinkable elastomeric film and said coverstock layer comprises a hydrophobic nonwoven material.

8. The absorbent article of claim 7 additionally comprises a pair of embossed channels in at least said absorbent core.

* * * * *